US011937932B2

(12) United States Patent
Wu et al.

(10) Patent No.: US 11,937,932 B2
(45) Date of Patent: Mar. 26, 2024

(54) ACUTE KIDNEY INJURY PREDICTING SYSTEM AND METHOD THEREOF

(71) Applicants: Taichung Veterans General Hospital, Taichung (TW); Tunghai University, Taichung (TW)

(72) Inventors: Chieh-Liang Wu, Taichung (TW); Chun-Te Huang, Taichung (TW); Cheng-Hsu Chen, Taichung (TW); Tsai-Jung Wang, Taichung (TW); Kai-Chih Pai, Taichung (TW); Chun-Ming Lai, Taichung (TW); Min-Shian Wang, Taichung (TW); Ruey-Kai Sheu, Taichung (TW); Lun-Chi Chen, Taichung (TW); Yan-Nan Lin, Taichung (TW); Chien-Lun Liao, Taichung (TW); Ta-Chun Hung, Taichung (TW); Chien-Chung Huang, Taichung (TW); Chia-Tien Hsu, Taichung (TW); Shang-Feng Tsai, Taichung (TW)

(73) Assignees: TAICHUNG VETERANS GENERAL HOSPITAL, Taichung (TW); TUNGHAI UNIVERSITY, Taichung (TW)

(*) Notice: Subject to any disclaimer, the term of this patent is extended or adjusted under 35 U.S.C. 154(b) by 0 days.

(21) Appl. No.: 17/860,908

(22) Filed: Jul. 8, 2022

(65) Prior Publication Data
US 2023/0380742 A1    Nov. 30, 2023

(30) Foreign Application Priority Data
May 25, 2022 (TW) ............................ 111119542

(51) Int. Cl.
*A61B 5/20* (2006.01)
*A61B 5/00* (2006.01)
*G16H 50/20* (2018.01)

(52) U.S. Cl.
CPC ............ *A61B 5/201* (2013.01); *A61B 5/7267* (2013.01); *A61B 5/7275* (2013.01); *G16H 50/20* (2018.01)

(58) Field of Classification Search
CPC ..... A61B 5/201; A61B 5/7267; A61B 5/7275; G16H 50/20
See application file for complete search history.

(56) References Cited

U.S. PATENT DOCUMENTS

2021/0183471 A1* 6/2021 Cha .................... G16H 50/30
2021/0398677 A1* 12/2021 Lanius ................. G06N 20/00

FOREIGN PATENT DOCUMENTS

| CN | 105144179 B | 5/2019 |
| CN | 104969071 B | 9/2019 |

(Continued)

OTHER PUBLICATIONS

Zhimeng Chen, et al.; "Analysis of the Impact of Medical Features and Risk Prediction of Acute Kidney Injury for Critical Patients Using Temporal Electronic Health Record Data with Attention-Based Neural Network"; Jun. 4, 2021; Frontiers in Medicine; vol. 8, Article 658665 (Year: 2021).*
Huang et al., "Entropy-Based Time Window Features Extraction for Machine Learning to Predict Acute Kidney Injury in ICU," Applied Sciences, (2021), vol. 11, issue 14, pp. 1-16, published by Multi-disciplinary Digital Publishing Institute, Switzerland.

*Primary Examiner* — Evangeline Barr
(74) *Attorney, Agent, or Firm* — McBee Moore & Vanik, IP, LLC (57) ABSTRACT

An acute kidney injury predicting system and a method thereof are proposed. A processor reads the data to be tested, the detection data, the machine learning algorithm and the risk probability comparison table from a main memory. The (Continued)

processor trains the detection data according to the machine learning algorithm to generate an acute kidney injury prediction model, and inputs the data to be tested into the acute kidney injury prediction model to generate an acute kidney injury characteristic risk probability and a data sequence table. The data sequence table lists the data to be tested in sequence according to a proportion of each of the data to be tested in the acute kidney injury characteristics. The processor selects one of the medical treatment data from the risk probability comparison table according to the acute kidney injury characteristic risk probability.

8 Claims, 7 Drawing Sheets

(56) References Cited

FOREIGN PATENT DOCUMENTS

| | | |
|---|---|---|
| CN | 110444263 A | 11/2019 |
| CN | 112885466 A | 6/2021 |
| CN | 114446470 A | 5/2022 |
| TW | I578262 B | 4/2017 |
| TW | M586446 U | 11/2019 |
| TW | 202111722 A | 3/2021 |
| TW | I755108 B | 2/2022 |

* cited by examiner

Fig. 1

Risk probability comparison table 240

- 241 Low risk treatment solution
  - Medical treatment data 2411
  - ⋮
  - Medical treatment data 2411
- 242 Moderate risk treatment solution
  - Medical treatment data 2421
  - ⋮
  - Medical treatment data 2421
- 243 High risk treatment solution
  - Medical treatment data 2431
  - ⋮
  - Medical treatment data 2431

| | |
|---|---|
| Diuretics | 0.176 |
| Total of nephrotoxic drugs | 0.167 |
| Norepinephrine | -0.132 |
| Proton pump inhibitor | 0.126 |
| Blood Urea Nitrogen | 0.065 |
| Dopamine | -0.064 |

ACUTE KIDNEY INJURY PREDICTING SYSTEM AND METHOD THEREOF

RELATED APPLICATIONS

This application claims priority to Taiwan Application Serial Number 111119542, filed May 25, 2022, which is herein incorporated by reference.

BACKGROUND

Technical Field

The present disclosure relates to a smart medical technology field. More particularly, the present disclosure relates to an acute kidney injury predicting system and a method thereof.

Description of Related Art

Acute Kidney Injury (AKI) is a common serious disease in the Intensive Care Unit (ICU), it is not easy to be diagnosed immediately. According to the survey, the prevalence of AKI in the ICU is estimated to be as high as 60%. In addition, the causes of AKI are complex and change rapidly, and how to grasp the timing of treatment is a great challenge for the health professionals in nephrology.

With the advancement of science and technology, Artificial Intelligence (AI) has gradually begun to be applied to image recognition and various medical diagnosis technologies. However, the prior machine learning models or deep learning models are obtained simply and directly by training the Electronic Health Record (EHR) of patient. Since the aforementioned training method does not consider the potential impact of missing data from EHR, it may lead to poor model performance or bias. In summary, there is still a lack of an acute kidney injury predicting system and a method thereof with high diagnostic accuracy that can immediately provide appropriate medical treatment, which are indeed highly anticipated by the public and become the goal and the direction of relevant industry efforts.

SUMMARY

According to one aspect of the present disclosure, an acute kidney injury predicting system is configured to predict an acute kidney injury characteristic risk probability corresponding to a plurality of data to be tested conforming to an acute kidney injury characteristic. The acute kidney injury predicting system includes a main memory and a processor. The main memory stores the data to be tested, a plurality of detection data, a machine learning algorithm and a risk probability comparison table, and the risk probability comparison table includes a plurality of medical treatment data. The processor is connected to the main memory and configured to implement an acute kidney injury predicting method including performing a data reading step, a model training step, a risk probability and sequence table generating step and a medical treatment data selecting step. The data reading step includes reading the data to be tested, the detection data, the machine learning algorithm and the risk probability comparison table. The model training step is performed to train the detection data according to the machine learning algorithm to generate an acute kidney injury prediction model. The risk probability and sequence table generating step is performed to input the data to be tested into the acute kidney injury prediction model to generate the acute kidney injury characteristic risk probability and a data sequence table. The data sequence table lists the data to be tested in sequence according to a proportion of each of the data to be tested in the acute kidney injury characteristic. The medical treatment data selecting step is performed to select one of the medical treatment data from the risk probability comparison table according to the acute kidney injury characteristic risk probability.

According to another aspect of the present disclosure, an acute kidney injury predicting method is configured to predict an acute kidney injury characteristic risk probability corresponding to a plurality of data to be tested conforming to an acute kidney injury characteristic. The acute kidney injury predicting method includes performing a data reading step, a model training step, a risk probability and sequence table generating step and a medical treatment data selecting step. The data reading step includes driving a processor to read the data to be tested, a plurality of detection data, a machine learning algorithm and a risk probability comparison table stored in a main memory. The risk probability comparison table includes a plurality of medical treatment data. The model training step includes driving the processor to train the detection data according to the machine learning algorithm to generate an acute kidney injury prediction model. The risk probability and sequence table generating step is performed to drive the processor to input the data to be tested into the acute kidney injury prediction model to generate the acute kidney injury characteristic risk probability and a data sequence table. The data sequence table lists the data to be tested in sequence according to a proportion of each of the data to be tested in the acute kidney injury characteristic. The medical treatment data selecting step is performed to drive the processor to select one of the medical treatment data from the risk probability comparison table according to the acute kidney injury characteristic risk probability.

BRIEF DESCRIPTION OF THE DRAWINGS

The present disclosure can be more fully understood by reading the following detailed description of the embodiment, with reference made to the accompanying drawings as follows.

DETAILED DESCRIPTION

The embodiment will be described with the drawings. For clarity, some practical details will be described below.

However, it should be noted that the present disclosure should not be limited by the practical details, that is, in some embodiment, the practical details is unnecessary. In addition, for simplifying the drawings, some conventional structures and elements will be simply illustrated, and repeated elements may be represented by the same labels.

It will be understood that when an element (or device) is referred to as be "connected to" another element, it can be directly connected to the other element, or it can be indirectly connected to the other element, that is, intervening elements may be present. In contrast, when an element is referred to as be "directly connected to" another element, there are no intervening elements present. Consequently, a first element or component discussed below could be termed a second element or component.

Figure 1:
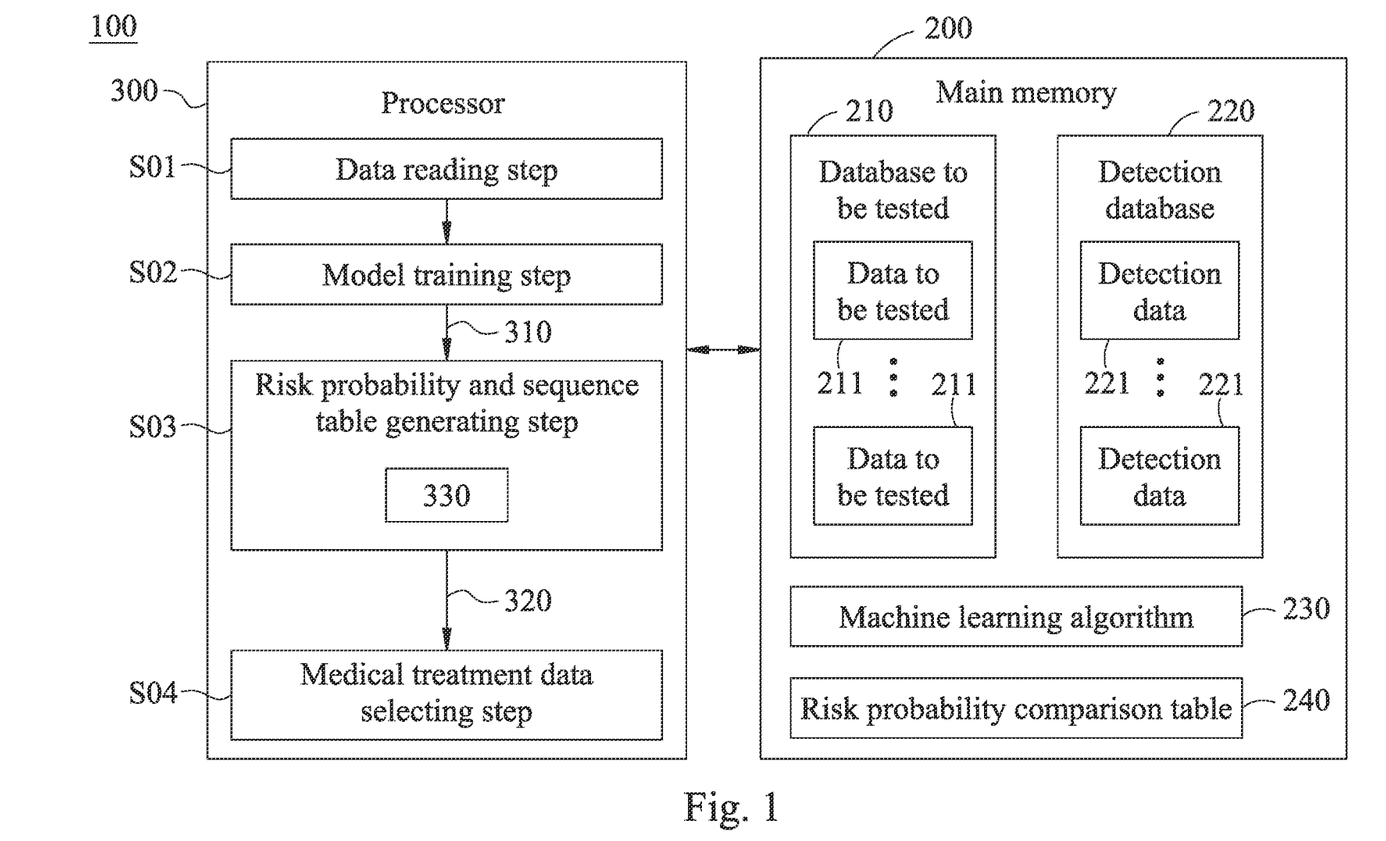
FIG. 1 shows a block diagram of an acute kidney injury predicting system according to a first embodiment of the present disclosure.
Figure 2:
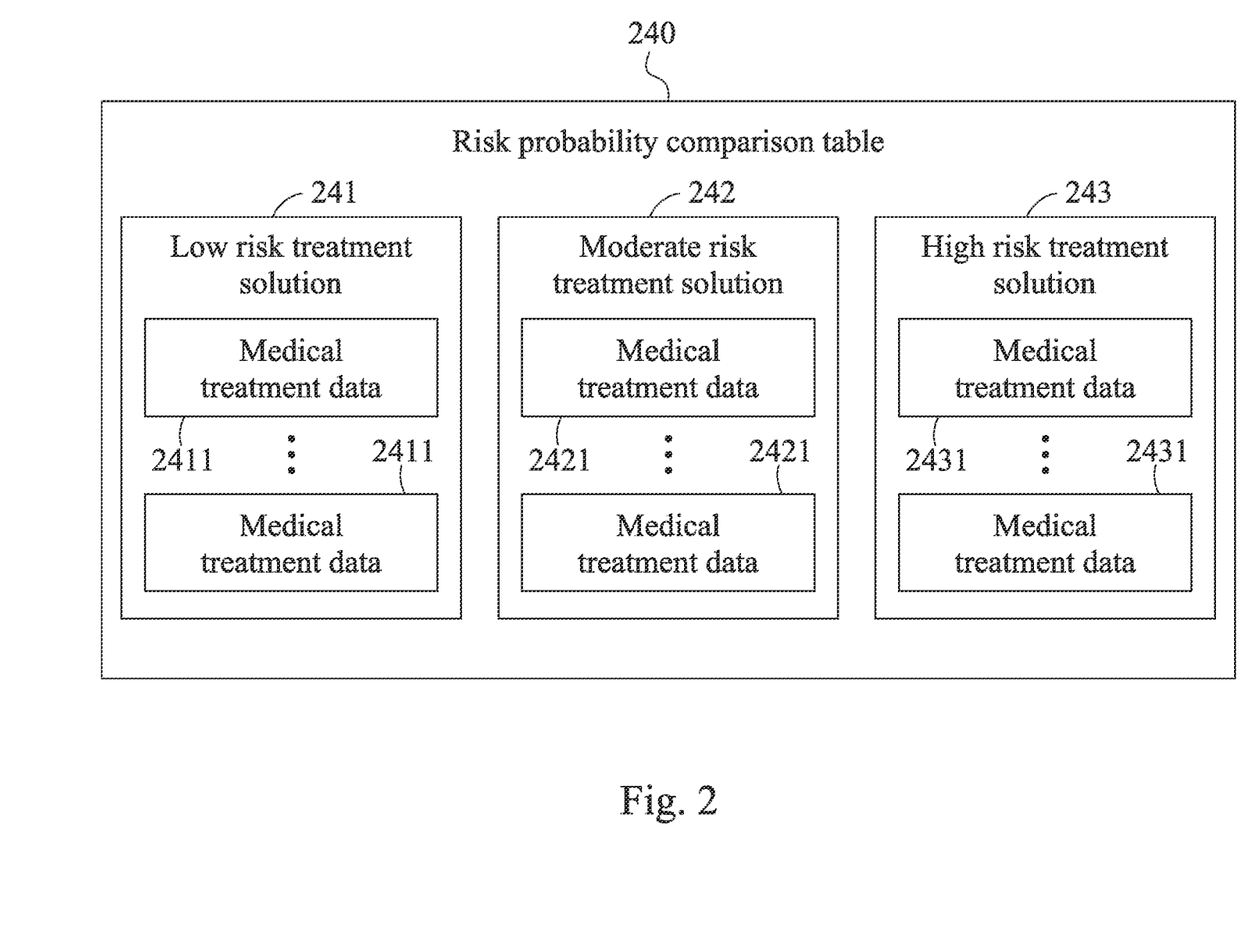
FIG. 2 shows a block diagram of a risk probability comparison table of the acute kidney injury predicting system of FIG. 1.

Please refer to FIGS. 1 and 2. FIG. 1 shows a block diagram of an acute kidney injury predicting system 100 according to a first embodiment of the present disclosure. FIG. 2 shows a block diagram of a risk probability comparison table 240 of the acute kidney injury predicting system 100 of FIG. 1. As shown in FIGS. 1 and 2, the acute kidney injury predicting system 100 includes a main memory 200 and a processor 300, and is configured to predict an acute kidney injury characteristic risk probability 320 corresponding to a plurality of data to be tested 211 conforming to an acute kidney injury characteristic after 24 hours. The acute kidney injury characteristic is determined by the conditions defined by Kidney Disease Improving Global Outcomes (KDIGO) for Acute Kidney Injury (AKI), and is not described again herein.

The main memory 200 stores a database to be tested 210, a detection database 220 for training model, a machine learning algorithm 230 and the risk probability comparison table 240. The database to be tested 210 includes the aforementioned plurality of the data to be tested 211, and the detection database 220 includes a plurality of detection data 221. The risk probability comparison table 240 includes a low risk treatment solution 241, a moderate risk treatment solution 242 and a high risk treatment solution 243. The low risk treatment solution 241 includes a plurality of medical treatment data 2411 applied when the acute kidney injury characteristic risk probability 320 is 0% to 49.99%. The moderate risk treatment solution 242 includes a plurality of medical treatment data 2421 applied when the acute kidney injury characteristic risk probability 320 is 50% to 74.99%. The high risk treatment solution 243 includes a plurality of medical treatment data 2431 applied when the acute kidney injury characteristic risk probability 320 is 75% to 100%.

The processor 300 is electrically connected to the main memory 200 and configured to implement an acute kidney injury predicting method including performing a data reading step S01, a model training step S02, a risk probability and sequence table generating step S03 and a medical treatment data selecting step S04. The data reading step S01 includes reading the data to be tested 211, the detection data 221, the machine learning algorithm 230 and the risk probability comparison table 240. The model training step S02 is performed to train the detection data 221 according to the machine learning algorithm 230 to generate an acute kidney injury prediction model 310. The risk probability and sequence table generating step S03 is performed to input the data to be tested 211 into the acute kidney injury prediction model 310 to generate the acute kidney injury characteristic risk probability 320 and a data sequence table 330. The data sequence table 330 lists the data to be tested 211 in sequence according to a proportion of each of the data to be tested 211 in the acute kidney injury characteristic. The medical treatment data selecting step S04 is performed to select one of the medical treatment data from the low risk treatment solution 241, the moderate risk treatment solution 242 and the high risk treatment solution 243 of the risk probability comparison table 240 according to the acute kidney injury characteristic risk probability 320. Therefore, the acute kidney injury predicting system 100 of the present disclosure utilizes the processor 300 to execute the data reading step S01, the model training step S02, the risk probability and sequence table generating step S03 and the medical treatment data selecting step S04 for generating the acute kidney injury characteristic risk probability 320 and the appropriate medical treatment data so as to achieve early prediction, diagnosis and treatment, and reduce the probability of the subject having AKI. At the same time, the acute kidney injury predicting system 100 of the present disclosure can suppress or shorten the disease process, and accelerate the recovery of kidney function to reduce the mortality rate, so that the overall medical quality of the severe cases is improved, and can share the pressure of clinical works and reduce the loading of the health professionals. The acute kidney injury predicting method of the present disclosure is described in more detail with the drawings and the embodiments below.

Figure 3:
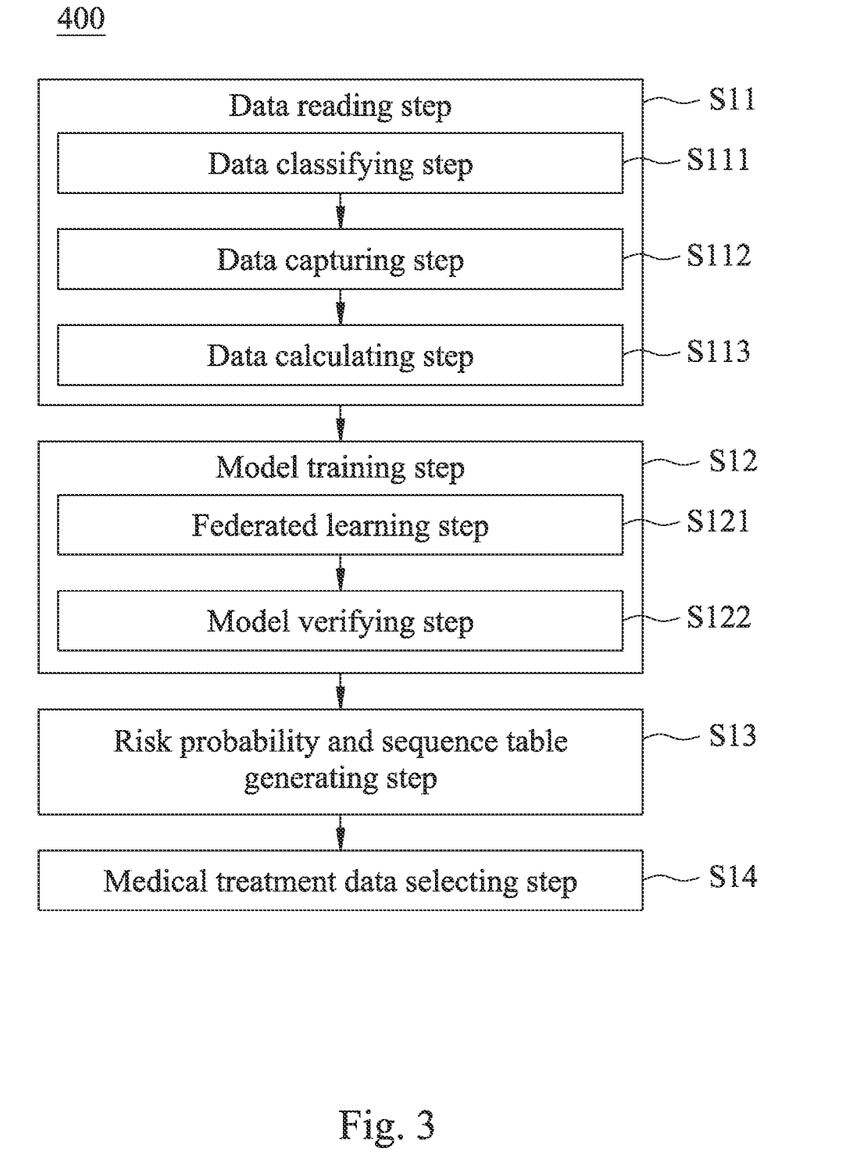
FIG. 3 shows a flow chart of an acute kidney injury predicting method according to a second embodiment of the present disclosure.

Please refer to FIGS. 1, 2 and 3. FIG. 3 shows a flow chart of the acute kidney injury predicting method 400 according to a second embodiment of the present disclosure. The acute kidney injury predicting method 400 is applied to the acute kidney injury predicting system 100, and includes performing a data reading step S11, a model training step S12, a risk probability and sequence table generating step S13 and a medical treatment data selecting step S14.

The data reading step S11 includes driving the processor 300 to read the data to be tested 211, the detection data 221, the machine learning algorithm 230 and the risk probability comparison table 240, which are stored in the main memory 200.

The model training step S12 includes driving the processor 300 to train the detection data 221 according to the machine learning algorithm 230 to generate the acute kidney injury prediction model 310. It should be noted that the machine learning algorithm 230 can be one of an eXtreme Gradient Boosting (XGBoost), a random forest, a neural network and a logistic regression, but the present disclosure is not limited thereto.

The risk probability and sequence table generating step S13 is performed to drive the processor 300 to input the data to be tested 211 into the acute kidney injury prediction model 310 to generate the acute kidney injury characteristic risk probability 320 and the data sequence table 330.

The medical treatment data selecting step S14 is performed to drive the processor 300 to select one of the medical treatment data from the low risk treatment solution 241, the moderate risk treatment solution 242 and the high risk treatment solution 243 of the risk probability comparison table 240 according to the acute kidney injury characteristic risk probability 320.

Figure 4:
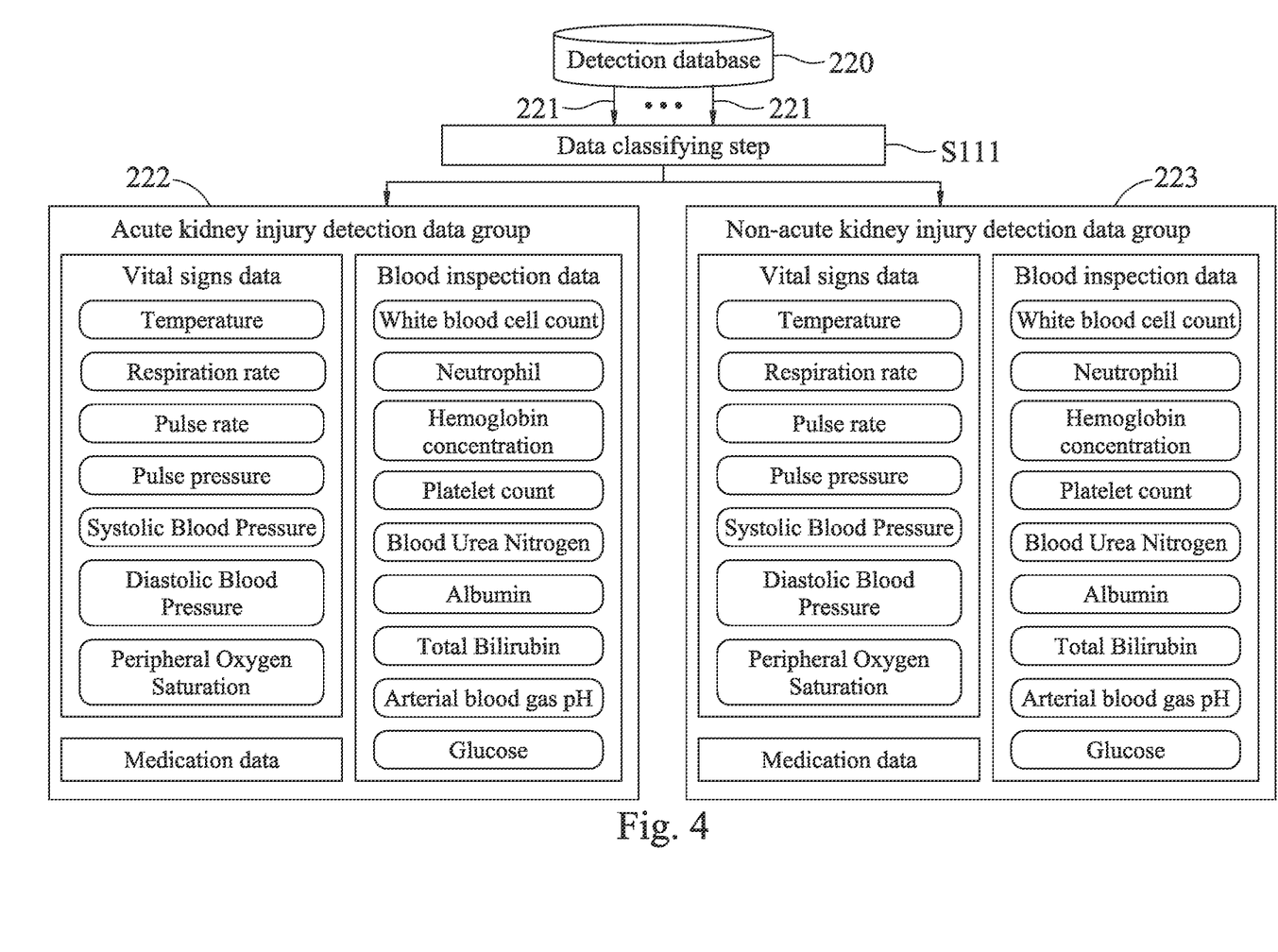
FIG. 4 shows a schematic view of a data classifying step of a data reading step of the acute kidney injury predicting method of FIG. 3.
Figure 5:
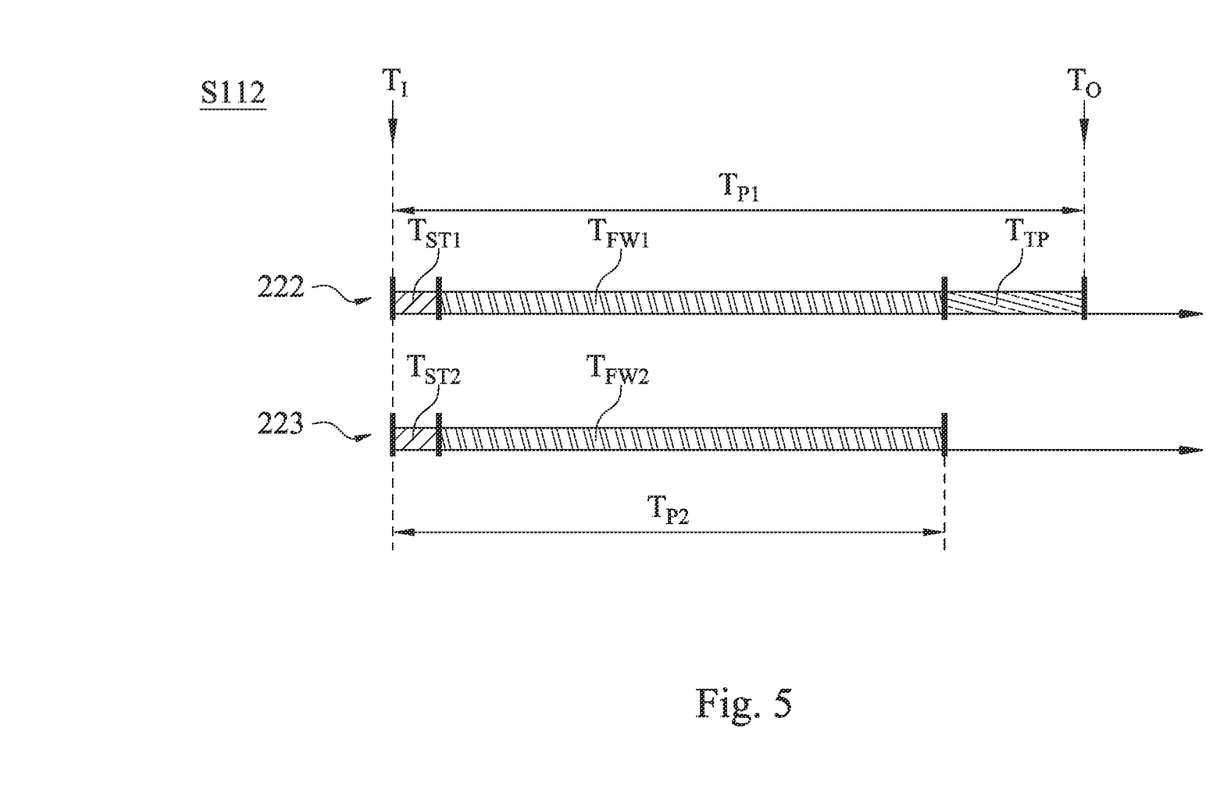
FIG. 5 shows a schematic view of a data capturing step of the data reading step of the acute kidney injury predicting method of FIG. 3.

Please refer to FIGS. 1, 3, 4 and 5. FIG. 4 shows a schematic view of a data classifying step S111 of the data reading step S11 of the acute kidney injury predicting method 400 of FIG. 3. FIG. 5 shows a schematic view of a data capturing step S112 of the data reading step S11 of the acute kidney injury predicting method 400 of FIG. 3. As shown in FIG. 3, the data reading step S11 of the acute kidney injury predicting method 400 can further include performing the data classifying step S111, the data capturing step S112 and a data calculating step S113.

As shown in FIG. 4, the data classifying step S111 is performed to drive the processor 300 to classify the detection data 221 of the detection database 220 into an acute kidney injury detection data group 222 and a non-acute kidney injury detection data group 223 according to an acute kidney injury standard. In particular, the acute kidney injury standard can be guidelines for AKI defined by KDIGO. The processor 300 determines whether the detection data 221 conforms to the acute kidney injury characteristic according to the acute kidney injury standard, and marks and distinguishes the detection data 221 into the acute kidney injury detection data group 222 with AKI and the non-acute kidney injury detection data group 223 without AKI. Moreover, the acute kidney injury detection data group 222 can include a plurality of vital signs data, a plurality of medication data and a plurality of blood inspection data. Each of the vital signs data can include a temperature, a respiration rate, a pulse rate, a pulse pressure, a Systolic Blood Pressure (SBP), a Diastolic Blood Pressure (DBP) and a Peripheral Oxygen Saturation ($SpO_2$). The medication data can be the specific drugs with a higher probability of AKI, which are selected from all drugs used in patients having AKI based on clinical experience. For example, the medication data can be Renin-angiotensin system inhibitors, Diuretics, Proton Pump Inhibitor (PPI), H2 Receptor Antagonists, NSAID-COX I inhibitors, COX II inhibitors, Vasopressin, Norepinephrine, Dopamine, Epinephrine, Dobutamine, Vancomycin, Bactrim, Gentamicin, Amikin, Colistin and Amphotericin B. Each of the blood inspection data can include a white blood cell count, a Neutrophil (NEUT), a hemoglobin concentration, a platelet count, a Blood Urea Nitrogen (BUN), an albumin, a Total Bilirubin (T-Bil), an arterial blood gas pH and a glucose. Similarly, the non-acute kidney injury detection data group 223 can also include the aforementioned medical routine data, and is not described again herein.

As shown in FIG. 5, the vital signs data of the acute kidney injury detection data group 222 are a plurality of medical parameter data (e.g., a plurality of temperature data) collected every minute in a time period $T_{P1}$, and the time period $T_{P1}$ is the time difference between the time of the AKI patient entering to the Intensive Care Unit (ICU) and the time of the AKI patient leaving the ICU. Accordingly, each of the vital signs data can have a timestamp, for example, the first temperature data corresponds to a first time, the second temperature data corresponds to a second time, and so on. The time period $T_{P1}$ includes an initial time point $T_I$, a data setting interval $T_{ST1}$, a feature window interval $T_{FW1}$, an early prediction interval $T_{TP}$, and a confirmed time point $T_O$. The data setting interval $T_{ST1}$ is a window period. Since the patient is admitted to the ICU at the initial time point $T_I$, it takes a setting period of time (i.e., the data setting interval $T_{ST1}$) to generate the vital signs data. The early prediction interval $T_{TP}$ is a time segment, which is a period before a time point (i.e., the confirmed time point $T_O$) when the patient is diagnosed with AKI. It is obvious that the feature window interval $T_{FW1}$ is located between the data setting interval $T_{ST1}$ and the early prediction interval $T_{TP}$. Further, the vital signs data of the non-acute kidney injury detection data group 223 are a plurality of medical parameter data collected every minute in a time period $T_{P2}$, and the time period $T_{P2}$ is the time difference between the time of the non-AKI patient entering to the ICU and the time of the non-AKI patient leaving the ICU. The time period $T_{P2}$ includes a data setting interval $T_{ST2}$ and a feature window interval $T_{FW2}$, and the data setting interval $T_{ST2}$ is the same as the data setting interval $T_{ST1}$. In FIG. 5, the time period $T_{P2}$ is smaller than the time period $T_{P1}$, but the time period $T_{P2}$ can be greater than the time period $T_{P1}$ in other embodiments; in short, the present disclosure is not limited to the time length of the feature window interval.

The data capturing step S112 is performed to drive the processor 300 to capture the vital signs data of the acute kidney injury detection data group 222 whose timestamps are located in the feature window interval $T_{FW1}$, and drive the processor 300 to capture the vital signs data of the non-acute kidney injury detection data group 223 whose timestamps are located in the feature window interval $T_{FW2}$. Specifically, the processor 300 divides the feature window interval $T_{FW1}$ into a plurality of sub-intervals according to a time interval (e.g., 6 hours), and captures the vital signs data of the acute kidney injury detection data group 222 in the sub-intervals. Since the vital signs data of the non-acute kidney injury detection data group 223 do not conform to the acute kidney injury characteristic, the processor 300 can arbitrarily capture the vital signs data of the non-acute kidney injury detection data group 223 in the feature window interval $T_{FW2}$.

Then, the data calculating step S113 is performed to drive the processor 300 to calculate the vital signs data whose the timestamps are located in the feature window interval $T_{FW1}$ to generate an average value and a variation value. Ultimately, in the model training step S12, the processor 300 trains the average value, the variation value, the medication data and the blood inspection data of the acute kidney injury detection data group 222 and the vital signs data, the medication data and the blood inspection data of the non-acute kidney injury detection data group 223 according to the machine learning algorithm 230 to generate the acute kidney injury prediction model 310. Therefore, the present disclosure performs the data preprocessing (i.e., the data capturing step S112 and the data calculating step S113) through the processor 300 to capture the vital signs data conforming to the acute kidney injury characteristic in the feature window interval $T_{FW1}$ to train the acute kidney injury prediction model 310, so that the data missing problem of the prior Electronic Health Record (EHR) is overcome, and the probability of predicting the acute kidney injury characteristic risk probability 320 corresponding to the data to be tested 211 conforming to the acute kidney injury characteristic after 24 hours is increased.

Figure 6:
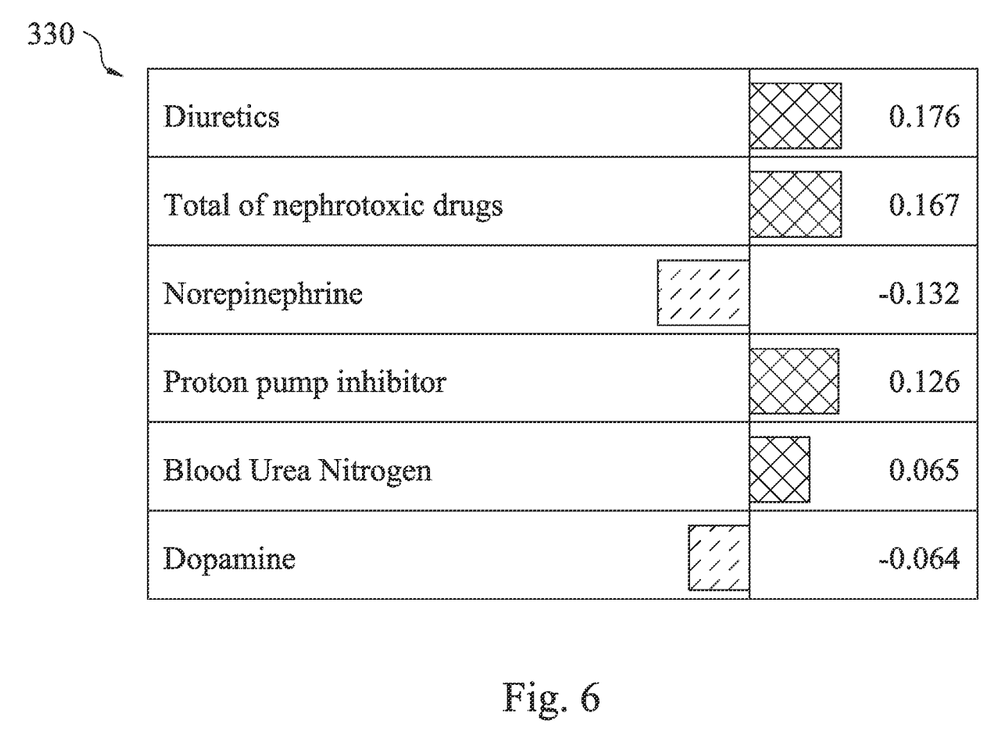
FIG. 6 shows a schematic view of a data sequence table of the acute kidney injury predicting method of FIG. 3.

Please refer to FIGS. 1, 3 and 6. FIG. 6 shows a schematic view of the data sequence table 330 of the acute kidney injury predicting method 400 of FIG. 3. In the risk probability and sequence table generating step S13, the data sequence table 330 lists the data to be tested 211 in sequence according to the proportion of each of the data to be tested 211 in the acute kidney injury characteristic. Specifically, the processor 300 lists the data to be tested 211 in sequence in the data sequence table 330 according to the proportion of each of the data to be tested 211 in the acute kidney injury characteristic through a characteristic numerical analysis (e.g., SHAP Value), and the data sequence table 330 can be displayed on the interface of the EHR system. For example, the data sequence table 330 in FIG. 6 lists six of the data to be tested 211 in sequence from top to bottom, which are Diuretics, the total of nephrotoxic drugs, Norepinephrine, Proton pump inhibitor (PPI), Blood Urea Nitrogen (BUN) and Dopamine. The present disclosure is not limited to the number of the data to be tested 211, which are listed in the data sequence table 330. Therefore, the acute kidney injury predicting method 400 of the present disclosure can offer the health professionals to judge the level of the patient conforming to the acute kidney injury characteristic by checking whether the important features in the front items of the data sequence table 330 have the administration of nephrotoxic drugs, and can also be used as a reference for clinical decision-making.

Figure 7:
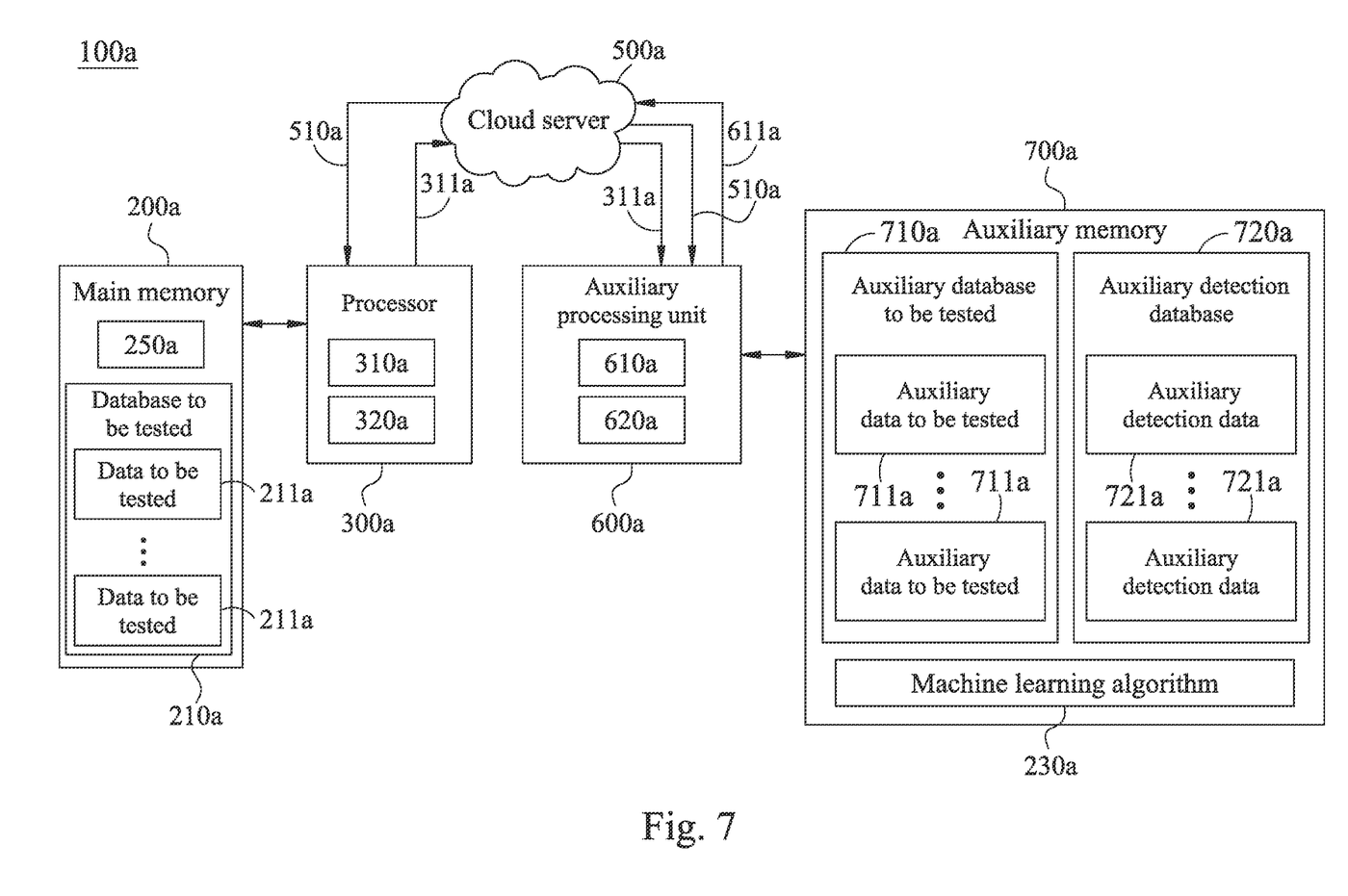
FIG. 7 shows a block diagram of an acute kidney injury predicting system according to a third embodiment of the present disclosure.

FIG. 7 shows a block diagram of an acute kidney injury predicting system 100a according to a third embodiment of the present disclosure. The acute kidney injury predicting system 100a includes a main memory 200a and a processor 300a. The main memory 200a and the processor 300a of the third embodiment are similar to the main memory 200 and the processor 300 of the first embodiment, respectively. The processor 300a generates an acute kidney injury prediction model 310a in the same method as the processor 300 of the first embodiment generating the acute kidney injury prediction model 310, and the method is not be described again herein.

The third embodiment differs from the first embodiment in that the acute kidney injury predicting system 100a can further include a cloud server 500a, an auxiliary processing unit 600a and an auxiliary memory 700a. The cloud server 500a is signally connected to the processor 300a. The processor 300a uploads a model parameter 311a of the acute kidney injury prediction model 310a to the cloud server 500a. The auxiliary memory 700a stores an auxiliary database to be tested 710a, a detection database 720a and a machine learning algorithm 230a. The auxiliary database to be tested 710a includes a plurality of auxiliary data to be tested 711a, the detection database 720a includes a plurality of auxiliary detection data 721a, and the machine learning algorithm 230a of the third embodiment is the same as the machine learning algorithm 230 of the first embodiment.

The auxiliary processing unit 600a is signally connected to the cloud server 500a and electrically connected to the auxiliary memory 700a. The auxiliary processing unit 600a downloads the model parameter 311a from the cloud server 500a and trains the model parameter 311a and the auxiliary detection data 721a according to the machine learning algorithm 230a to generate an auxiliary acute kidney injury prediction model 610a. The auxiliary processing unit 600a uploads an auxiliary model parameter 611a of the auxiliary acute kidney injury prediction model 610a to the cloud server 500a, and the cloud server 500a aggregates the model parameter 311a and the auxiliary model parameter 611a to create another acute kidney injury prediction model 510a. The processor 300a downloads the acute kidney injury prediction model 510a from the cloud server 500a, and replaces the acute kidney injury prediction model 310a with the acute kidney injury prediction model 510a. The processor 300a inputs a plurality of data 211a to be tested of a database 210a to be tested stored in the main memory 200a into the acute kidney injury prediction model 510a to generate an acute kidney injury characteristic risk probability 320a. The processor 300a verifies whether the acute kidney injury characteristic risk probability 320a conforms to a real outcome 250a stored in the main memory 200a. It should be noted that the real outcome 250a can be a diagnosis result obtained after the data 211a to be tested has been diagnosed by the health professional. In response to determining that the acute kidney injury characteristic risk probability 320a does not conform to the real outcome 250a, the cloud server 500a reaggregates the model parameter 311a and the auxiliary model parameter 611a to update the acute kidney injury prediction model 510a, until the acute kidney injury characteristic risk probability 320a conforms to the real outcome 250a.

In addition, the acute kidney injury predicting method 400 of the second embodiment can also be applied to the acute kidney injury predicting system 100a of the third embodiment, and the model training step S12 of the acute kidney injury predicting method 400 can further include performing a federated learning step S121 and a model verifying step S122 (as shown in FIG. 3).

The federated learning step S121 is performed to drive the processor 300a to upload the model parameter 311a of the acute kidney injury prediction model 310a to the cloud server 500a for the auxiliary processing unit 600a to download the model parameter 311a from the cloud server 500a and train the model parameter 311a and the auxiliary detection data 721a of the detection database 720a stored in the auxiliary memory 700a according to the machine learning algorithm 230a to generate the auxiliary acute kidney injury prediction model 610a. The auxiliary processing unit 600a uploads the auxiliary model parameter 611a of the auxiliary acute kidney injury prediction model 610a to the cloud server 500a, and the cloud server 500a aggregates the model parameter 311a and the auxiliary model parameter 611a to create the acute kidney injury prediction model 510a.

The model verifying step S122 is performed to drive the processor 300a to download the acute kidney injury prediction model 510a from the cloud server 500a and replace the acute kidney injury prediction model 310a with the acute kidney injury prediction model 510a, and then the processor 300a inputs the data 211a to be tested of the database 210a to be tested stored in the main memory 200a into the acute kidney injury prediction model 510a to generate the acute kidney injury characteristic risk probability 320a. The processor 300a verifies whether the acute kidney injury characteristic risk probability 320a conforms to the real outcome 250a stored in the main memory 200a. In response to determining that the acute kidney injury characteristic risk probability 320a does not conform to the real outcome 250a, the cloud server 500a reaggregates the model parameter 311a and the auxiliary model parameter 611a to update the acute kidney injury prediction model 510a, until the acute kidney injury characteristic risk probability 320a in next time conforms to the real outcome 250a.

In detail, the level of the medical institutions can be divided into a medical center, a regional hospital, a district hospital and a primary clinic. The medical institutions have different levels of care tasks and work projects. For example, the medical center is responsible for research, teaching and the treatment and care of critically ill patients. Hence, in the same as the ICU, the medical center belongs to an evacuation hospital of the regional hospital and the district hospital, so the patients of the medical center in the ICU have higher disease severity than the other medical institutions. The processor 300a of the acute kidney injury predicting system 100a can correspond to the aforementioned medical center, and the auxiliary processing unit 600a can correspond to the lower-level medical institution.

The present disclosure enables the processor 300a and the auxiliary processing unit 600a to perform a federated learning through the federated learning step S121, and utilizes the real outcome 250a to verify the acute kidney injury characteristic risk probability 320a generated by the acute kidney injury prediction model 510a having aggregated. For example, in response to determining that the real outcome 250a indicates that the patient has suffered from AKI, and the acute kidney injury characteristic risk probability 320a is assumed to be 85%. The processor 300a sets a morbidity range (e.g., 80% to 100%) and verifies whether the acute kidney injury characteristic risk probability 320a conforms to the real outcome 250a according to the morbidity range. Since the acute kidney injury characteristic risk probability 320a still remains within the morbidity range, the processor 300a determines that the acute kidney injury characteristic risk probability 320a is consistent with the real outcome 250a. On the contrary, if the acute kidney injury characteristic risk probability 320a is 75%, the processor 300a verifies whether the acute kidney injury characteristic risk probability 320a conforms to the real outcome 250a according to the morbidity range. Since the acute kidney injury characteristic risk probability 320a exceeds the morbidity range, the processor 300a determines that the acute kidney injury characteristic risk probability 320a does not conform to the real outcome 250a. Subsequently, the processor 300a will repeatedly perform the federated learning step S121, and utilizes the acute kidney injury prediction model 510a having aggregated in next time to recheck the data 211a to be tested until the acute kidney injury characteristic risk probability 320a in the next time conforms to the real outcome 250a. Further, the auxiliary processing unit 600a can also download the acute kidney injury prediction model 510a having aggregated, and input the auxiliary data to be tested 711a of the auxiliary database to be tested 710a stored in the auxiliary memory 700a into the acute kidney injury prediction model 510a to generate an auxiliary acute kidney injury characteristic risk probability 620a.

Therefore, the acute kidney injury prediction model 510a is generated through the cross-hospital cooperation performed by the cloud server 500a, so that the acute kidney injury prediction model 510a having aggregated can be used not only in a single medical institution. In addition, in other embodiments, the number of the auxiliary processing units can be plural, and the present disclosure is not limited thereto.

In summary, the present disclosure has the following advantages. First, the acute kidney injury characteristic risk probability and the medical treatment data is used to achieve early prediction, diagnosis and treatment, and reduce the probability of the subject having AKI. At the same time, it is favorable to suppress or shorten the disease process and accelerate the recovery of kidney function to reduce the mortality rate, so that the overall medical quality of the severe cases is improved, and can share the pressure of clinical works and reduce the loading of the health professionals. Second, the acute kidney injury prediction model is trained by performing the data preprocessing to capture the vital signs data conforming to the acute kidney injury characteristic in the feature window interval, so that the data missing problem of the prior EHR is overcome, and the probability of predicting the acute kidney injury characteristic risk probability corresponding to the data to be tested conforming to the acute kidney injury characteristic after 24 hours is increased. Third, the acute kidney injury prediction model is updated or replaced through the cross-hospital cooperation of the federated learning, so that the acute kidney injury prediction model having aggregated in the cloud server is not limited to the single medical institution.

Although the present disclosure has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present disclosure without departing from the scope or spirit of the disclosure. In view of the foregoing, it is intended that the present disclosure cover modifications and variations of this disclosure provided they fall within the scope of the following claims.

What is claimed is:

1. An acute kidney injury predicting system, which is configured to predict an acute kidney injury characteristic risk probability corresponding to a plurality of data to be tested conforming to an acute kidney injury characteristic, and the acute kidney injury predicting system comprising:
a main memory storing the data to be tested, a plurality of detection data, a machine learning algorithm and a risk probability comparison table, wherein the risk probability comparison table comprises a plurality of medical treatment data; and
a processor connected to the main memory and configured to implement an acute kidney injury predicting method comprising:
performing a data reading step, wherein the data reading step comprises reading the data to be tested, the detection data, the machine learning algorithm and the risk probability comparison table;
performing a model training step to train an acute kidney injury prediction model by using the detection data according to the machine learning algorithm;
performing a risk probability and sequence table generating step to input the data to be tested into the acute kidney injury prediction model to generate the acute kidney injury characteristic risk probability and a data sequence table, wherein the data sequence table lists the data to be tested in sequence according to a proportion of each of the data to be tested in the acute kidney injury characteristic; and
performing a medical treatment data selecting step to select one of the medical treatment data from the risk probability comparison table according to the acute kidney injury characteristic risk probability;
wherein the data reading step further comprises:
performing a data classifying step to drive the processor to classify the detection data into an acute kidney injury detection data group and a non-acute kidney injury detection data group according to an acute kidney injury standard, wherein the acute kidney injury detection data group comprises a plurality of vital signs data, a plurality of medication data and a plurality of blood inspection data;
wherein the vital signs data of the acute kidney injury detection data group are collected every minute in a time period between a patient entering to an intensive care unit and the patient leaving the intensive care unit, the time period comprises a data setting interval, a feature window interval and an early prediction interval, the feature window interval is located between the data setting interval and the early prediction interval, each of the vital signs data of the acute kidney injury detection data group has a timestamp, and the data reading step further comprises:
performing a data capturing step to drive the processor to capture the vital signs data of the acute kidney injury detection data group whose timestamps are located in the feature window interval; and
performing a data calculating step to drive the processor to calculate the vital signs data of the acute kidney injury detection data group whose the timestamps are located in the feature window interval to generate an average value and a variation value;
wherein in the model training step, the processor trains the acute kidney injury prediction model by using the average value, the variation value, the medication data and the blood inspection data of the acute kidney injury detection data group and the non-acute kidney injury detection data group according to the machine learning; wherein the machine learning algorithm is an eXtreme Gradient Boosting (XGBoost).

2. The acute kidney injury predicting system of claim 1, wherein each of the vital signs data comprises a temperature, a respiration rate, a pulse rate, a pulse pressure, a Systolic Blood Pressure (SBP), a Diastolic Blood Pressure (DBP) and a Peripheral Oxygen Saturation (SpO$_2$).

3. The acute kidney injury predicting system of claim 1, wherein each of the blood inspection data comprises a white blood cell count, a Neutrophil (NEUT), a hemoglobin concentration, a platelet count, a Blood Urea Nitrogen (BUN), an albumin, a Total Bilirubin (T-Bil), an arterial blood gas pH and a glucose.

4. The acute kidney injury predicting system of claim 1, further comprising:
a cloud server connected to the processor, wherein the processor uploads a model parameter of the acute kidney injury prediction model to the cloud server;
an auxiliary memory storing a plurality of auxiliary detection data, a plurality of auxiliary data to be tested and the machine learning algorithm; and
an auxiliary processing unit connected to the cloud server and the auxiliary memory and downloading the model parameter from the cloud server, wherein the auxiliary processing unit trains the model parameter and the auxiliary detection data according to the machine learning algorithm to generate an auxiliary acute kidney injury prediction model and uploads an auxiliary model parameter of the auxiliary acute kidney injury prediction model to the cloud server, and the cloud server aggregates the model parameter and the auxiliary model parameter to create another acute kidney injury prediction model;
wherein the processor downloads the another acute kidney injury prediction model from the cloud server and inputs the data to be tested into the another acute kidney injury prediction model to generate another acute kidney injury characteristic risk probability, and the processor verifies whether the another acute kidney injury characteristic risk probability conforms to a real outcome;
wherein in response to determining that the another acute kidney injury characteristic risk probability does not conform to the real outcome, the cloud server reaggregates the model parameter and the auxiliary model parameter to update the another acute kidney injury prediction model, until the another acute kidney injury characteristic risk probability conforms to the real outcome.

5. An acute kidney injury predicting method, which is configured to predict an acute kidney injury characteristic risk probability corresponding to a plurality of data to be tested conforming to an acute kidney injury characteristic, and the acute kidney injury predicting method comprising:
performing a data reading step, wherein the data reading step comprises driving a processor to read the data to be tested, a plurality of detection data, a machine learning algorithm and a risk probability comparison table stored in a main memory, wherein the risk probability comparison table comprises a plurality of medical treatment data;
performing a model training step, wherein the model training step comprises driving the processor to train an acute kidney injury prediction model by using the detection data according to the machine learning algorithm;
performing a risk probability and sequence table generating step to drive the processor to input the data to be tested into the acute kidney injury prediction model to generate the acute kidney injury characteristic risk probability and a data sequence table, wherein the data sequence table lists the data to be tested in sequence according to a proportion of each of the data to be tested in the acute kidney injury characteristic; and
performing a medical treatment data selecting step to drive the processor to select one of the medical treatment data from the risk probability comparison table according to the acute kidney injury characteristic risk probability;
wherein the data reading step further comprises:
performing a data classifying step to drive the processor to classify the detection data into an acute kidney injury detection data group and a non-acute kidney injury detection data group according to an acute kidney injury standard, wherein the acute kidney injury detection data group comprises a plurality of vital signs data, a plurality of medication data and a plurality of blood inspection data;
wherein the vital signs data of the acute kidney injury detection data group are collected every minute in a time period between a patient entering to an intensive care unit and the patient leaving the intensive care unit, the time period comprises a data setting interval, a feature window interval and an early prediction interval, the feature window interval is located between the data setting interval and the early prediction interval, each of the vital signs data of the acute kidney injury detection data group has a timestamp, and the data reading step further comprises:
performing a data capturing step to drive the processor to capture the vital signs data of the acute kidney injury detection data group whose timestamps are located in the feature window interval; and
performing a data calculating step to drive the processor to calculate the vital signs data of the acute kidney injury detection data group whose the timestamps are located in the feature window interval to generate an average value and a variation value;
wherein in the model training step, the processor trains the acute kidney injury prediction model by using the average value, the variation value, the medication data and the blood inspection data of the acute kidney injury detection data group and the non-acute kidney injury detection data group according to the machine learning algorithm;
wherein the machine learning algorithm is an eXtreme Gradient Boosting (XGBoost).

6. The acute kidney injury predicting method of claim 5, wherein each of the vital signs data comprises a temperature, a respiration rate, a pulse rate, a pulse pressure, a Systolic Blood Pressure (SBP), a Diastolic Blood Pressure (DBP) and a Peripheral Oxygen Saturation (SpO$_2$).

7. The acute kidney injury predicting method of claim 5, wherein each of the blood inspection data comprises a white blood cell count, a Neutrophil (NEUT), a hemoglobin concentration, a platelet count, a Blood Urea Nitrogen (BUN), an albumin, a Total Bilirubin (T-Bil), an arterial blood gas pH and a glucose.

8. The acute kidney injury predicting method of claim 5, wherein the model training step further comprises:

performing a federated learning step to drive the processor to upload a model parameter of the acute kidney injury prediction model to a cloud server for an auxiliary processing unit to download the model parameter from the cloud server, wherein the auxiliary processing unit trains the model parameter and a plurality of auxiliary detection data stored in an auxiliary memory according to the machine learning algorithm stored in the auxiliary memory to generate an auxiliary acute kidney injury prediction model and uploads an auxiliary model parameter of the auxiliary acute kidney injury prediction model to the cloud server, and the cloud server aggregates the model parameter and the auxiliary model parameter to create another acute kidney injury prediction model; and performing a model verifying step to drive the processor to download the another acute kidney injury prediction model from the cloud server and input the data to be tested into the another acute kidney injury prediction model to generate another acute kidney injury characteristic risk probability, wherein the processor verifies whether the another acute kidney injury characteristic risk probability conforms to a real outcome;

wherein in response to determining that the another acute kidney injury characteristic risk probability does not conform to the real outcome, the processor repeatedly performs the federated learning step, until the another acute kidney injury characteristic risk probability conforms to the real outcome.

* * * * *